United States Patent [19]

Lewiner et al.

[11] E Patent Number: Re. 32,180

[45] Reissued Date of Patent: Jun. 10, 1986

[54] COMPOSITE SHEETS CONSTITUTING ELECTROMECHANICAL TRANSDUCERS AND TRANSDUCERS EQUIPPED WITH SUCH SHEETS

[76] Inventors: Jacques Lewiner, 5 rue Bory d'Arnex, 92210 Saint Cloud; Claude Hennion, 18, rue Flatters, 75005 Paris, both of France

[21] Appl. No.: 672,139

[22] Filed: Nov. 15, 1984

Related U.S. Patent Documents

Reissue of:

[64] Patent No.: 4,359,726
Issued: Nov. 16, 1982
Appl. No.: 228,716
Filed: Jan. 27, 1981

[30] Foreign Application Priority Data

Feb. 12, 1980 [FR] France ..... 8003093

[51] Int. Cl.[4] ..... G08B 21/00

[52] U.S. Cl. ..... 340/573; 307/400; 310/800; 340/666; 128/721; 128/782

[58] Field of Search ..... 340/666, 573; 200/85 A, 200/85 R, 86 A, 86 R; 310/800, 338; 307/400; 128/782, 721, 712, 671

[56] References Cited

U.S. PATENT DOCUMENTS

| | | | |
|---|---|---|---|
| 3,794,790 | 2/1974 | Leyland | 200/85 A |
| 3,798,474 | 4/1982 | Cassand et al. . | |
| 3,809,828 | 5/1974 | Haugsjaa et al. | 307/400 |
| 3,836,900 | 9/1974 | Mansfield | 340/666 |
| 3,926,177 | 12/1975 | Hardway, Jr. et al. | 340/573 |
| 3,944,763 | 3/1976 | Beierwaltes | 200/86 R |
| 3,991,746 | 11/1976 | Hanna | 340/573 |
| 3,996,922 | 12/1976 | Basham | 307/400 |
| 4,110,741 | 8/1978 | Hubert et al. | 340/573 |
| 4,156,800 | 5/1979 | Sear et al. | 310/800 |

*Primary Examiner*—Glen R. Swann, III
*Attorney, Agent, or Firm*—Larson and Taylor

[57] ABSTRACT

[The invention relates to a flexible composite sheet designed to constitute an undersheet behaving as an electromechanical transducer in order to detect the apnea of subjects lying on it. This sheet comprises, in addition to a foil sensitive to pressure in the sense of electromechanical transduction (an electret or polarized piezoelectric foil), two film electrodes and two protective foils. Spacing shims are glued to the two foils against which they are juxtaposed. When the sensitive foil is an electret, the shims are directly interposed between the sensitive foil and one of the two electrodes. When the sensitive foil is a polarized piezo-electric foil, the shims are directly interposed between one of the electrodes and the corresponding external protective foil.] *An apnea monitor/alarm consists of an electronic monitor circuit to actuate an alarm responsive to the output of a sheet-like electromechanical transducer. The transducer consists of an electret or polarized piezoelectric foil responsive to pressure to generate corresponding electrical signals, two film electrodes, and two protective foils. Shims are glued to two of the foils for spacing. If an electret sensor foil is used, the shims are directly interposed between the sensitive foil and one of the electrodes. If the sensitive foil is a polarized piezoelectric foil, the shims are directly interposed between one of the electrodes and the corresponding external protective foil.*

28 Claims, 4 Drawing Figures

Fig.1.
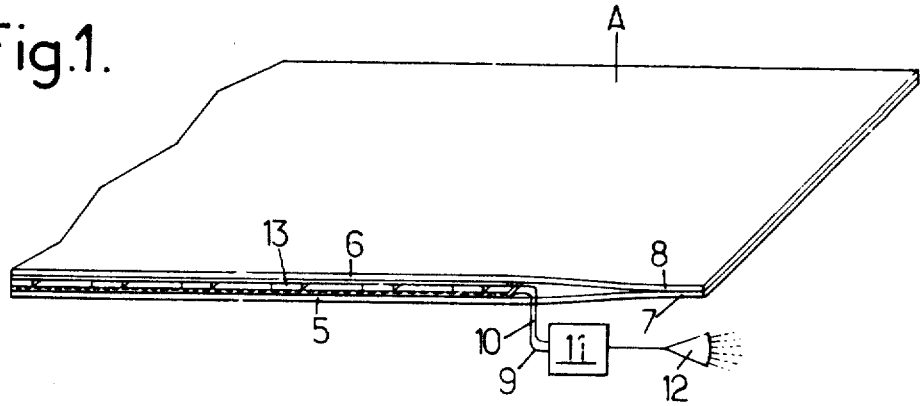
Fig.2.
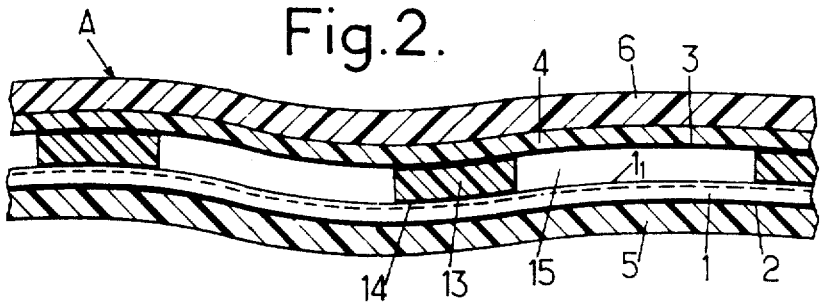
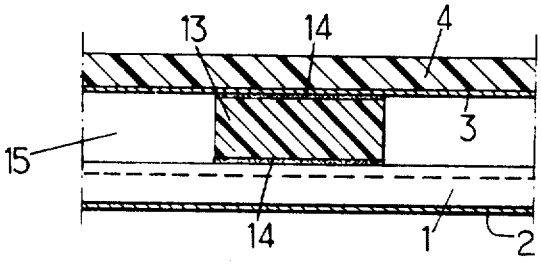
Fig.3.
Fig.4.
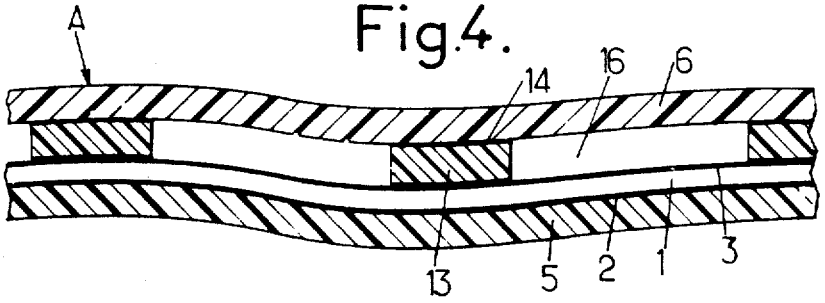

COMPOSITE SHEETS CONSTITUTING ELECTROMECHANICAL TRANSDUCERS AND TRANSDUCERS EQUIPPED WITH SUCH SHEETS

Matter enclosed in heavy brackets [ ] appears in the original patent but forms no part of this reissue specification; matter printed in italics indicates the additions made by reissue.

BACKGROUND OF THE INVENTION

The invention relates to composite sheets constituting electromechanical transducers and more particularly those, of these sheets, which have a certain flexibility and extend over a relatively large area, this area being preferably of the order of several square decimeters.

The invention is also directed to transducers equipped with such composite sheets.

It is known that these transducers permit the transformation into variations of an electrical voltage, of the pressure variations which are exerted locally on the sheet and/or the local deformations of this sheet.

The composite sheets concerned comprise essentially for this purpose a dielectric foil "sensitive" to pressure in the sense of electromechanical transduction, which foil is permanently electrically charged or carries a permanent electrical polarisation, interposed between two electrodes or electrically conducting films themselves covered externally with two protective foils, and the transducers equipped with these composite sheets include, in addition to the latter, electrical exploitation means and possibly warning means connected to the two electrodes of said composite sheets.

An interesting application of these transducers, to which the invention relates preferably, but not exclusively, is the detection of apnea, the monitoring of the biologic functions (respiration, cardiac rhythm, . . . ), particularly in nurslings.

Draw-sheets or undersheets are constituted for this purpose, by means of the composite sheets concerned, which are interposed between a mattress and the subject to be watched, lying down, sitting or supported on the mattress: the respiratory movements of this subject cause cyclic local variations in the pressure exterted on this draw-sheet, which variations are manifested by similar cyclic variations of an electrical voltage, and the exploitation means are arranged so as to activate the alarm when said cyclic variations of voltage cease for a time which exceeds a threshold estimated as dangerous or having a form differing excessively from a form considered as normal.

It is a particular object of the invention to improve the fidelity and reliability of transducers of the type concerned.

GENERAL DESCRIPTION OF THE INVENTION

To this end, composite sheets of the above type are essentially characterized in that they comprise, between the sensitive foil and one of the protective foils, separating shims of which the two opposite surfaces are glued respectively to the two adjacent facing areas.

In preferred embodiments, recourse is had in addition to one and/or the other of the following features:

in the case where the sensitive foil is permanently electrically charged and creates an external electrical field, the shims are directly interposed between this sensitive foil and one of the two electrodes, which forms chambers bounded by this electrode, this sensitive foil and these shims, in the case where the sensitive foil is a permanently electrically polarized piezo-electrical foil and interposed contiguously between the two electrodes, the shims are directly interposed between one of these electrodes and the corresponding external protective foil, which forms chambers bounded by this electrode, this protective foil and these shims, the shims are made self-adhesive on their two surfaces, the areas to which the shims are glued are previously treated so as to facilitate this adhesion, notably by electronic or ionic bombardment, or again by the deposition of a thin layer of a material, such as chromium, offering a good grip to the glues, the shims are constituted by a grid, the shims are constituted by a perforated continuous foil, the shims are constituted by parallel strips, the shims are constituted by spaced studs, the shims have a thickness comprised between 0.1 and 1 mm, a width comprised between 1 and 10 mm and a mutual spacing comprised between 5 and 100 mm, the composite sheet constitutes a rectangular undersheet for nurslings of which one of the sides is comprised between 10 and 30 cm and the other side between 20 and 50 cm.

The invention comprises, apart from these main features, certain other features which are preferably used at the same time and which will be more explicitly considered below.

In the following, two preferred embodiments of the invention will be described with reference to the accompanying drawings, given, of course, as non-limiting Examples.

BRIEF DESCRIPTION OF THE DRAWINGS

FIG. 1 of these drawings, shows in perspective view, with portions broken away, one embodiment of a draw-sheet constructed according to the invention.

FIG. 2 shows on a larger scale, in cross-section, a portion of this draw-sheet.

FIG. 3 shows on a still larger scale, in cross-section, a detail of said portion.

FIG. 4 shows similarly to FIG. 2 a modification of a portion of a draw-sheet also according to the invention.

DESCRIPTION OF PREFERRED EMBODIMENTS

Included in the pad or draw-sheet A is a dielectric foil 1 interposed between two foils, films or elecrically conducting layers 2 and 3, denoted below by the word "electrodes".

The foil 1 is selected so that it is "sensitive" in the sense of electromechanical transduction, that is to say that it is capable of converting the pressure variations applied locally to it into variations of the electrical voltage collected at the terminals of the two electrodes 2 and 3.

To this end, foil 1 is advantageously constituted of a plastics material such as polypropylene, P.T.F.E., poly(fluorinated ethylene-propylene) or again a polymer or copolymer based on polyvinylidene fluoride, its thickness being preferably comprised between 5 and 50 microns.

This foil 1 is permanently electrically polarized or is permanently electrically charged at least in the vicinity of $1_1$ of its surfaces, by positive and/or negative charges which are shown diagrammatically by the sign—in FIG. 2.

In the latter case (permanent electrical charge), the foil 1 creates an external electrical field and it is kept separated, at least in part, from one of the electrodes 3 by insulating gaps, as is visible in FIG. 2.

In the other case (permanent electrical polarization), shown diagrammatically in FIG. 4, the foil 1 possesses piezo-electrical properties and it is contiguously enveloped by the two electrodes 2 and 3.

Each of the electrodes 2 and 3 is advantageously constituted by surface metallization of a foil of plastics material.

In the case of the charged sensitive foil (FIG. 2), one 2 of these electrodes is attached to this foil 1 whilst the other electrode 3, held slightly separated from said foil 1 by any desirable means, is attached to an additional plastics foil 4.

In the case of the polarized sensitive foil 1 (FIG. 4), the two electrodes 2 and 3 are attached respectively to the two surfaces of this foil 1.

The assembly of the three foils 1, 2 and 3 is itself positioned between two external protective foils 5 and 6, whose thickness is advantageously comprised between 0.1 and 0.5 mm, constituted of an electrically insulating flexible material.

These protective foils 5 and 6 extend beyond the assembly of the three foils 1, 2 and 3 and their projecting margins 7 and 8 (FIG. 1) are assembled against one another so as to provide a seal with respect to impurities, notably by gluing or heat welding.

The draw-sheet A, formed by the flexible sheet composed of the superposed foils 1, 2, 3, 5 and 6, has the general shape of a rectangle whose sides measure repectively between 10 and 30 cm and between 20 and 50 cm when used as a draw-sheet for nurslings.

Each of the electrodes 2 and 3 is connected by means of leads 9 and 10 to a suitable exploitation or output unit 11—advantageously of an electronic type with C-MOS circuits—adapted to activate a sound, visual or the like alarm device 12.

For the application of the pad or draw-sheet A concerned with the detection of apnea of a subject resting of this draw-sheet, the activation of the warning system 12 is automatically ensured when the oscillations, of the voltage between the electrodes 2 and 3, due to the normal respiration of said subject, are interruped for a period longer than a predetemined threshold, which can be adjusted at will and can be equal, for example, to 10 or 30 seconds or have a form departing to an excessive extent from a form considered as normal.

There is provided, in addition, according to the invention, a plurality of separating shims 13 interposed between the sensitive foil 1 and one, 6, of the outer protective foils, the two opposite surfaces of the shims being glued respectively to the areas of foil against which they are juxtaposed.

The shims 13 concerned may be formed of any desirable shapes and materials.

They can be in the form of grids or trellises formed from flat crossed elements united preferably at their crossing points so as not to create local overthicknesses, or again in the form of a perforated continuous foil, or in that of parallel flat strips, or of spaced flat studs, of square, rectangular, circular of the like cross-section.

Their constituent material may be insulating or electrically conducting: it is then selected so that the shims do not run the risk of tearing the flexible foils against which they are glued.

With this same aim of avoiding such tears, it will be advantageous in certain cases to avoid too sharp edges or points on the shims.

The dimensions of these shims 13, considered in a plane perpendicular to that of the composite sheet such as that in which FIG. 3 is traced, are preferably comprised between 0.1 and 1 mm for the thickness, between 1 and 10 mm for the width, and between 5 and 100 mm for the mutual spacing.

The gluing of the shims 13 against the facing foil areas is ensured by means of a thin layer of adhesive material 14.

Such a layer is advantageously applied in advance on each shim 13 surface, for example by spraying, so that the positioning of these shims may be very easily effected by self-adhesion.

In view of their very slight thicknesses, for example of the order of some tenths of microns, the electrodes 2, 3 and adhesive layers 14 have been represented by thick lines in FIG. 2 and 4: FIG. 3 on a larger scale enables them to be seen best.

To facilitate the gluing of the shims 13 to the facing foil areas, it may be advantageous to treat these areas previously, notably by electronic or ionic (electrical discharge) bombardment, or again by local deposition (under vacuum or otherwise) of a thin layer of a material, such as chromium, offering good compatibility with the glues.

In the first embodiment relating to the use of a charged sensitive foil 1, which has been illustrated in FIGS. 2 and 3, the shims 13 are directly inserted between the charged surface $1_1$ of this foil and the facing electrode 3: it is these shims which hold surface $1_1$ spaced from the electrode 3 and bound between them well defined chambers or compartments 15.

In the second embodiment relating to the use of a polarised piezoelectric foil 1, which has been illustrated in FIG. 4, the shims 13 are interposed directly between one, 3, of the electrodes attached against this foil 1 and the corresponding protective foil 6, again defining between these elements well defined chambers or compartments 16.

In each case, the double gluing of the shims according to the invention ensures a particularly accurate operation of the transducer:

in the first case, it is certain that the variations of the distance between the charged surface $1_1$ and the facing electrode 3 are due exclusively to the deformations, of this electret and/or of this electrode, which develope at the level of the different compartments 15 defined between successive shims: in other words, there is no question here that the individual distortions exploited for monitoring purposes involve surface portions, of the composite sheet, covering pluralities of neighbouring shims, even variable numbers of such shims, as would be the case if there were a possiblity of ungluing between these shims and the areas of the foil against which they are juxtaposed;

in the second case, the pressure variations exerted locally on the foil 1 are manifested by elastically reversible depressions of the portions, of this foil, positioned opposite the compartments 16, within these compartments, which lengthens, and hence thins these portions: it is especially these reversible thinnings which are converted into electrical variations exploited for monitoring purposes; due to the gluing concerned, said thinnings correspond only the depressions indicated whereas an absence of gluing of the shims would make possible slippages of the foil along these shims, able to denature the characteristics of these depressions.

As is itself evident, and as emerges besides from the foregoing, the invention is in no way limited to those of its methods of application and embodiments which have been more especially contemplated; it encompasses, on the contrary, all modifications.

In particular, the spacing shims could be formed by molding with one of the foils against which they are intended to be glued, constituting, for example, projecting ribs on the inner surface in FIG. 4.

In the same way, the spacing shims could be arranged so as to permit a flow of air on the outside of the composite sheet to the cavities 15 and in the reverse direction.

Similarly, any one of the two composite structures described above could be double:

it would be possible for this purpose to let comprise in common the electrode 3 of FIG. 2 by two structures of the type illustrated in said FIG. 2 and to apply symetrically two shim-electret-other electrode-protective foil assemblies to respectively the two surfaces of this electrode 3, the latter then being itself splitable and constituted by metallisation of the two surfaces of the additional foil 4, it would also be possible to apply to each of the surfaces of the shims 13 of FIG. 4 the assembly of a foil 1 metallised on its two surfaces and coated externally with a protective sheet.

In each of these two latter modifications, the two outer electrodes of the "doubled" structure obtained may be connected together and constitute an electrostatic shielding for the composite sheet.

In another modification, the various layers of the composite sheet may be constituted of transparent materials, so that the composite sheet is itself transparent.

In another modification, the electrodes 2 and 3 are divided into several electrically disjointed areas, so as to permit localisation on the composite sheet of the region which is deformed and where the pressure is exerted.

We claim:

1. Relatively flexible and extended composite sheet, constituting an electromechanical transducer and comprising a foil sensitive to pressure in the sense of electromechanical transduction, said pressure sensitive foil being interposed between two conductive foils or electrodes themselves covered exeternally with protective foils, said composite sheet also comprising, between the pressure sensitive foil and one of the protective foils, spacing shims of which the two opposite surfaces are glued respectively to the two opposite adjacent areas.

2. Sheet according to claim 1, wherein the sensitive foil is permanently electrically charged and creates an external electrical field, and the shims are directly interposed between said sensitive foil and one of the two electrodes.

3. Sheet according to claim 1, wherein the sensitive foil comprises a piezo-electric foil permanently electrically polarized and interposed contiguously between the two electrodes, the shims are directly interposed between one of these electrodes and the corresponding external protective foil.

4. Sheet according to claim 1, wherein the shims re self-adhesive on the said surfaces.

5. Sheet according to claim 1, wherein the areas on which the shims are glued are treated previously so as to facilitate this gluing.

6. Sheet according to claim 5, wherein said previous treatment is by electrical discharge.

7. Sheet according to claim 5, wherein said previous treatment comprises deposition of a thin layer of a suitable substance for enhancing said gluing.

8. Sheet according to claim 1, wherein the shims have a thickness comprised between 0.1 and 1 mm, a width comprised between 1 and 10 mm and a mutual spacing comprised between 5 and 100 mm.

9. Rectangular mattress construction incorporating a composite sheet according to claim 1, whose sides are comprised respectively between 10 and 30 cm and between 20 and 50 cm.

10. Sheet according to claim 1, wherein the various layers are constituted of transparent materials.

11. Electromechanical transducer comprising a composite sheet according to claim 1, and output means connected electrically to the two electrodes of said sheet.

12. Electrochemical transducer according to claim 11, including alarm means connected to said output means so as to activated thereby.

*13. An Apnea monitor comprising:*

*a composite sheet of sufficient area to underlie a baby comprising:*

*a piezoelectric foil;*

*electrodes covering opposite surfaces of said piezoelectric foil;*

*cover layers overlying each of said electrodes; and*

*spacing means, located between one of said cover layers and the corresponding electrode and affixed to said one cover layer and said corresponding electrode at a plurality of locations, for providing a plurality of compartments between said one cover layer and said corresponding electrode such that portions of the piezoelectric foil which lie adjacent these compartments will be reversibly lengthened when a pressure force is applied to the composite sheet at the corresponding compartments, said compartments being distributed substantially uniformly over the area of said piezoelectric foil; and*

*a monitor means, connected to said electrodes, for monitoring electrical signals produced in response to changes in the piezoelectric foil, whereby rhythmic movements of a baby will rhythmically lengthen and relax said portions of said piezoelectric foil so as to produce an electrical signal in response to said rhythmic movements which is monitored by said monitor means.*

*14. An Apnea monitor as claimed in claim 13, wherein said monitor means includes alarm means for producing an alarm output when the electrical signal monitored by said monitor means is interrupted for a period longer than a predetermined threshold period.*

*15. An Apnea monitor comprising:*

*a sheet of piezoelectric foil of sufficient area to underlie a baby;*

*electrodes covering opposite surfaces of said foil;*

*means providing a spaced shim support for portions of said foil while leaving other portions unsupported, and shim support being adhesively secured to one of the electrodes;*

*the unsupported portions being distributed substantially uniformly over the area of said foil;*

*a monitor;*

*and leads connecting said electrodes to said monitor;*

*whereby the biological functions of a baby will rhythmically lengthen and relax said unsupported portions of said foil to produce a signal, corresponding to said biological functions, on said electrodes which is transmitted to said monitor.*

*16. A monitor for monitoring biological movements of a living being, said monitor comprising:*

*(a) a composite sheet comprising:*

*a relatively flexible piezoelectric foil:*

*a pair of electrode members located on opposite sides of said piezoelectric foil;*

*a cover member overlying at least one of said electrode members; and*

*spacing means, located between the piezoelectric foil and one of said members, for providing a plurality of spaces between said piezoelectric foil and said one member such that a portion of the piezoelectric foil which lies adjacent a said space will be reversibly lengthened and thinned when a pressure force is applied to said composite sheet at the corresponding space; and*

*(b) a monitor means, connected to said electrodes, for monitoring electrical signals produced in response to changes in the piezoelectric foil whereby biological movements of the living being will lengthen and relax at least some of said portions of said piezoelectric foil so as to produce an electrical signal in response to said movements which is monitored by said monitor means.*

*17. A monitor as claimed in claim 16 wherein at least one surface of said spacing means is secured to the surface adjacent thereto.*

*18. A monitor as claimed in claim 16 wherein said electrode members comprise metallic foils secured to opposite surfaces of said piezoelectric foil and said cover member comprises a protective foil, said spacing means being secured to one of said electrode foils and to said protective foil.*

*19. A monitor as claimed in claim 16 wherein said spaces comprises chambers distributed substantially uniformly over the area of said piezoelectric foil.*

*20. A monitor as claimed in claim 16, wherein said monitor means includes alarm means for producing an alarm output when the electrical signal monitored by said monitor means is interrupted for a period longer than a predetermined threshold period.*

*21. A monitor for monitoring the movements of a living being, said monitor comprising:*

*(a) an electromechanical transducer comprising:*

*a relatively flexible piezoelectric foil;*

*a pair of electrode members located on opposite sides of said piezoelectric foil; and*

*space defining means for defining a plurality of spaces adjacent portions of said piezoelectric foil such that a said portion of the piezoelectric foil will be reversibly depressed and lengthened when a pressure force is applied to the transducer at the corresponding space; and*

*(b) a monitor means, connected to said electrodes, for monitoring electrical signals produced in response to changes in the piezoelectric foil whereby movements of the living being will reversibly lengthen said portions of said piezoelectric sheet so as to produce an electrical signal in response to said movements for monitoring by said monitor means.*

*22. A monitor as claimed in claim 21 wherein said transducer comprises a composite sheet and said space defining means comprise spacing shim means for spacing said piezoelectric foil from one component of said composite sheet so as to define said spaces therebetween.*

*23. A monitor as claimed in claim 22, wherein said one component comprises a cover sheet which overlies one of said electrodes.*

*24. In a monitor for monitoring the biological movements of a living being, a transducer comprising:*

*a piezoelectric foil;*

*an electrode on each side of said foil, and*

*means for creating reversible depressions in said foil at selected positions distributed around the area of said foil in response to biological stimuli produced by a living being in contact with said film.*

*25. A transducer according to claim 24 in which said depression creating means comprises:*

*shim means underlying said piezoelectric foil, said shim means creating a chamber at each of said selected locations under the piezoelectric foil into which a portion of said foil can be depressed in response to stimuli produced by a living being in contact with said transducer on the side of said transducer remote from said shim means.*

*26. A transducer according to claim 25 further comprising:*

*a protective sheet surrounding a composite formed by said foil, said electrodes and said shim means;*

*and means for affixing said shim means to at least one of said elements of said composite and to said protective sheet.*

*27. A method of monitoring biological functions of a living body comprising the steps of:*

*placing against a portion of the living body a transducer comprising a piezoelectric foil having electrodes on each surface thereof and having shim means distributed over the surface of said foil for creating a plurality of locations at which portions of said foil can be reversibly lengthened and thinned;*

*and utilizing the voltage generated between said electrodes responsive to the reversibly thinning of said foil at least one of said locations so as to monitor biological functions of the living body.*

*28. A monitor for monitoring the movements of a living being, said monitor comprising:*

*(a) a relatively flexible transducer composite comprising:*

*an electret foil;*

*electrodes located on opposite sides of said electret foil;*

*a protective cover overlying at least one said electrodes; and*

*spacing means, affixed to the components of said composite lying adjacent thereto at a plurality of locations, for providing a plurality of compartments within said composite such that when a pressure force is applied to the composite at the corresponding compartments, the portions of the electret foil which lie adjacent these compartments produce an electrical output; and*

*(b) monitor means, connected to said electrodes, for monitoring electrical signals produced by said electret foil, whereby movements of a living being will cause pressure forces to be applied to said portions of said electret foil so as to produce a resultant electrical output signal in response to said movements which is monitored by said monitor means.*

* * * * *